United States Patent [19]
Horn

[11] 4,325,256
[45] Apr. 20, 1982

[54] OPTICAL BICHROMATIC POSITION FINDER

[75] Inventor: Michael Horn, Sound Beach, N.Y.

[73] Assignee: Optsonic Research Associates, Ltd., New York, N.Y.

[21] Appl. No.: 216,567

[22] Filed: Dec. 15, 1980

Related U.S. Application Data

[62] Division of Ser. No. 102,241, Dec. 10, 1979, Pat. No. 4,275,596.

[51] Int. Cl.³ .............................................. G01N 29/00
[52] U.S. Cl. ........................................ 73/607; 73/618; 73/633
[58] Field of Search ........................ 73/607, 618, 633; 33/1 PT, 1 M, 1 N; 356/138, 403

[56] References Cited

U.S. PATENT DOCUMENTS

| | | | |
|---|---|---|---|
| 3,410,956 | 11/1968 | Grossman et al. | 33/1 M |
| 3,799,678 | 3/1974 | Kerr | 33/1 M |
| 3,918,814 | 11/1975 | Weiser | 356/138 |
| 3,932,039 | 1/1976 | Frey | 356/138 |

*Primary Examiner*—Anthony V. Ciarlante
*Attorney, Agent, or Firm*—Ostrolenk, Faber, Gerb & Soffen

[57] ABSTRACT

A method and apparatus for determining the position of a sensor with respect to a color screen are disclosed. The screen is colored with first and second colors in such a way that the intensity of each color varies from a minimum to maximum along a respective direction lying in the plane of the screen, the two respective directions being oblique to each other. As a result, each point on the screen is characterized by a unique pair of color intensities. The sensor is provided with means for measuring the intensity of each color at the point on the colored surface corresponding to the location of the sensor. In one advantageous application of the invention, one surface of a screen is colored as described above, and the screen is placed over an object to be ultrasonically inspected. The ultrasonic scanner is provided with color intensity measurement means and can be made to automatically scan the entire object being tested without intervention by the operator, the resulting data being stored and processed by a microprocessor or other suitable means.

7 Claims, 7 Drawing Figures

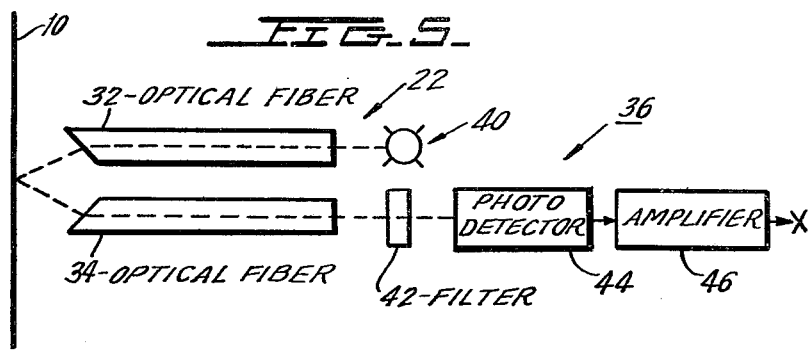
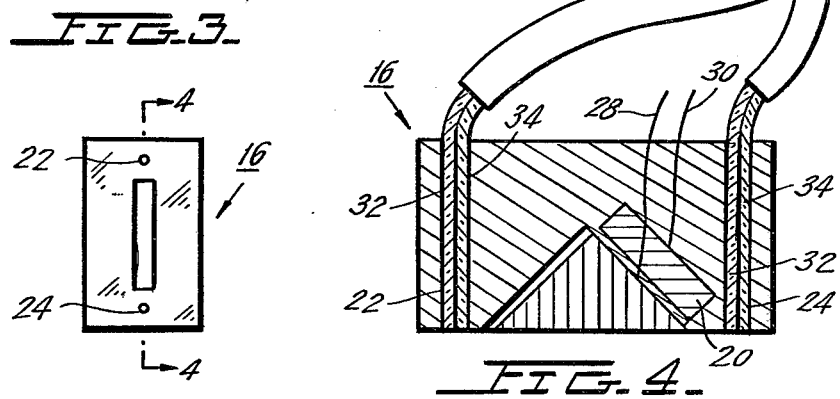
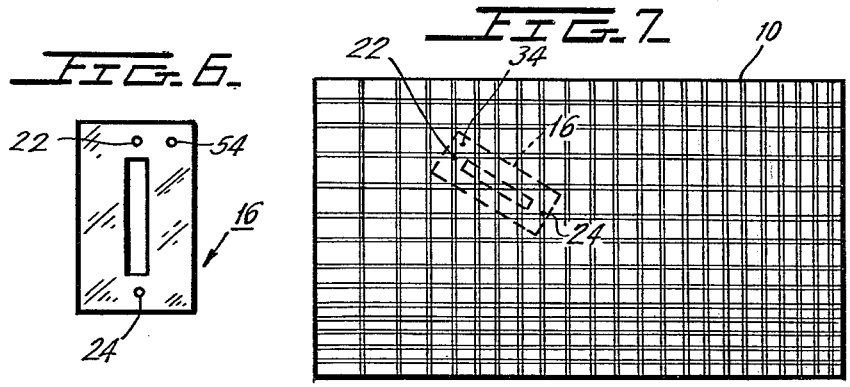

OPTICAL BICHROMATIC POSITION FINDER

RELATED APPLICATIONS

This is a divisional of U.S. patent application Ser. No. 102,241 filed Dec. 10, 1979 now U.S. Pat. No. 4,275,596.

BACKGROUND OF THE INVENTION

This application pertains to a device for determining the lateral location of an object with respect to a two-dimensional surface. More particularly, it pertains to a device for determining positions by measuring various optical characteristics of the two-dimensional surface.

In some industrial processes it is necessary to monitor the exact position of one object (normally a scanning sensor) with respect to another (normally an object being scanned). One example of such a process is inspecting a weldment by ultrasonically scanning the volume containing it. In such a process, an ultrasonic source is moved from one position to another adjacent one surface of the volume containing the weldment to be inspected. At each position, ultrasonic waves are emitted and the reflections from the workpiece are analyzed and interpreted to provide the desired information as to the quality of the weldment. Various examples of such a method are given in detail in McMasters, *Non-Destructive Testing Handbook,* Library of Congress No. 59-14660 (1959), especially pages 43-33 through 43-37 and 46-1 through 46-25, the disclosure of which is incorporated herein by reference. The use of the locating device of the present invention will be described herein with reference to such an ultrasonic scanning system. It should be recognized, however, that the use of the invention is not so limited and the invention may be used in connection with any system which requires information concerning the location of one object (normally a scanning sensor) with respect to a second scanning object (normally an object being scanned).

Ultrasonic techniques in use at present commonly require manual positioning of an ultrasonic source at each of many points with respect to the volume to be inspected, interpretation of the results obtained at each location, and documentation of the results. Only an extremely skilled operator can successfully obtain an accurate depiction of an internal defect in a workpiece being examined. Results are nearly always uncertain, since there is no guarantee that all of a weld has been explored. For these reasons, presently available field-operated ultrasonics equipment is not adequate for evaluating a new surface comprehensively and can only be used to monitor in-service deterioration.

Radioscopic examination, the common alternative to ultrasonics testing, has its own severe disadvantages. X-ray testing is very time consuming, requiring set up time for each exposure, time to clear the area of personnel before making the exposure, and time for developing and interpreting the exposure. In order to minimize radiation danger to personnel, X-ray inspection is generally carried out at night, requiring higher pay for the operator; in addition, night-time operation requires the operators to work in pairs for safety and results in less supervisory control of the inspection process. Moreover, X-ray films are bulky, hard to store, and costly and deteriorate relatively rapidly. In addition, an extremely high level of skill is required to interpret the exposures. For all of these reasons, radioscopic inspection is extremely expensive.

SUMMARY OF THE INVENTION

It is accordingly one object of the present invention to provide means for determining the location of an object with respect to a two-dimensional surface.

It is another object to provide means for monitoring not only the location but also the angular orientation of an object with respect to a two-dimensional surface.

It is still another object to provide such means that can be used in conjunction with a microprocessor or otherwise to make an ultrasonic scan and a permanent record of a weldment or other internal structure of a solid body.

It is yet a further object to attain these ends cheaply, simply and efficiently.

According to one preferred embodiment of the present invention, a two-dimensional screen is printed with each of two colors, preferably complimentary colors. The intensity of one color varies uniformly from a minimum to a maximum along one direction on the screen, while the intensity of the other color varies uniformly from a minimum to a maximum along a second direction oblique to the first direction. An object to be moved over the surface of the screen and whose position with respect to the screen is to be monitored, is provided with color intensity measuring units, each of which measures the color intensity of one of the two colors in the region of the screen nearest the object. Each of the color intensity measurement units is provided with an appropriate filter so that it measures the intensity of only one of the two colors with which the screen is printed. Since the combination of the respective values of the intensities of the two colors is unique for each point of the screen, measurement of the intensities permits exact determination of the location of the object.

Other features and advantages of the present invention will become clearer upon consideration of the following detailed description taken in conjunction with the accompanying Figures.

In the following description, reference is made to an ultrasonic scanning system. While this represents the presently preferred use of the position locating system of the present invention, it should be recognized that the invention is not so limited and that any use of the position locating system falls within the broad scope of the invention.

BRIEF DESCRIPTION OF THE FIGURES

For the purpose of illustrating the invention, there are shown in the drawings several embodiments which are presently preferred; it is to be understood, however, that this invention is not limited to the precise arrangements and instrumentalities shown.

FIG. 3 is a bottom view of the ultrasonic sensor unit having two light transmission paths, which system forms part of the system shown schematically in FIG. 2.

FIG. 4 is a cross-sectional view of the ultrasonic sensor unit of FIG. 3 taken along section line 4—4 of FIG. 3.

FIG. 5 is a schematic view of a color detector which is used in conjunction with the system of FIG. 2.

FIG. 6 is a view similar to FIG. 3 of an ultrasonic sensor unit having three light transmission paths to permit determination of the angular orientation of the unit.

FIG. 7 is a schematic view of a screen of the present invention showing the manner in which a threechannel device of the type shown in FIG. 5 can be used to determine angular orientation.

DETAILED DESCRIPTION OF THE INVENTION

Figure 1:
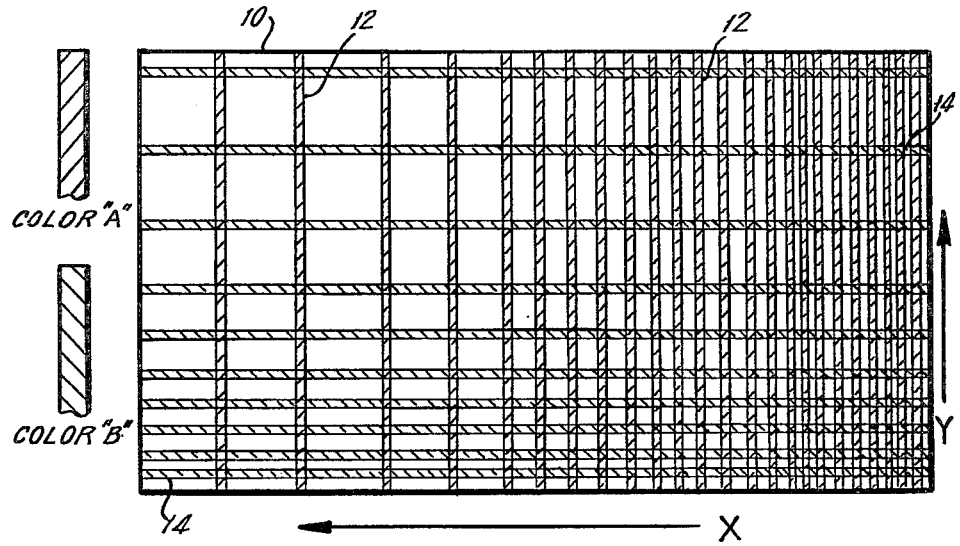
FIG. 1 is a schematic front view of a bichromatic screen according to the present invention.

Referring now to the drawings, wherein like numerals indicate like elements, FIG. 1 shows a bichromatic screen 10 according to the present invention, which provides a system of coordinates by means of which the exact location of any point on the surface of the screen 10 can be exactly specified. One color, color A, is printed on the surface of the screen with an intensity which preferably, but not necessarily, varies uniformly from a maximum to a minimum along the X direction. The pigmentation of color A is represented by the cross-hatched vertical bars 12 whose horizontal spacing increases from the right-hand to the left-hand end of the screen. A second color B, preferably complementary to color A, is also printed on the screen surface, its intensity varying uniformly from a maximum to a minimum along a direction Y oblique to direction X. This is shown schematically by the cross-hatched horizontal bars 14. In the illustrated embodiment, directions X and Y are perpendicular, and each corresponds to a major axis of the rectangular screen. It should be recognized, however, that directions X and Y may have any relation as long as they are not parallel, that neither direction needs to correspond to a principal axis of the screen, and that the screen can have any convenient shape. It should also be noted that although the varying intensity of color A is represented by bars 12 of color A lying perpendicular to the X direction and being disposed with a linear density in the X direction that varies from one end of the screen to the other, the varying intensity of color B being similarly indicated, in actual practice the manner of obtaining the required variable densities is not critical. The particular colors used are also not critical. Black, while technically not a color, can also be used.

Figure 2:
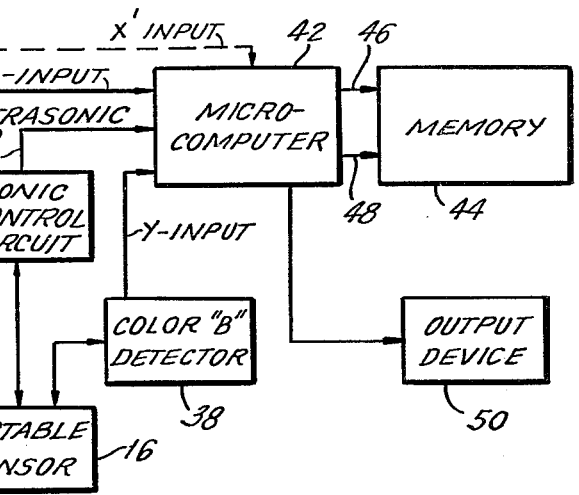
FIG. 2 is a schematic diagram of an ultrasonic scanning system utilizing the location determining apparatus of the present invention.
Figure 2:
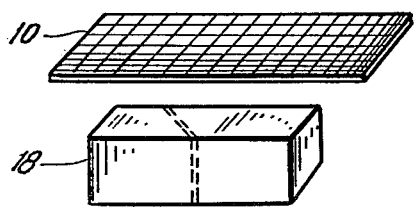

As noted above, the primary object of the present invention is to make it possible to determine the location of a portable sensor 16 with respect to the bichromatic screen 10. By locating the screen 10 at a predetermined disposition with respect to an object to be ultrasonically scanned, it is possible to move the sensor 16 across the screen 10 and at all times determine the location of the sensor 16 with respect to the object being scanned. This relationship is illustrated in FIG. 2. As shown therein, the screen 10 is located between the volume 18 whose internal structure is to be scanned and the ultrasonic sensor 16. The spacing between the sensor 16, bichromatic screen 10 and volume 18 has been exaggerated in order to separately illustrate the three elements. In practice, the bichromatic screen 10 will normally be placed in contact with the outer surface of volume 18 and the sensor 16 will be moved across the face of screen 10 in contact therewith.

The preferred structure of portable sensor 16 is illustrated in FIGS. 3 and 4. FIG. 3 is a bottom view of portable sensor 16 while FIG. 4 is a cross-sectional view taken along line 4—4 of FIG. 3. As best viewed in FIG. 4, sensor 16 includes an ultrasonic transducer 20 and a pair of light transmission paths 22, 24. Transducer 20 is coupled to a sonic control circuit 26 via a pair of conductive leads 28, 30. The sonic control circuit generates impulse signals which are applied to transducer 20 and which cause transducer 20 to establish shear mode or suitable mode sonic waves in the volume 18. Sonic control circuit 26 also receives echo information from transducer 20 and converts this information into a sonic echo signal indicative of the internal structure of volume 18. By way of example, sonic control circuit 26 will measure the time interval between the instant in which it applies a drive pulse to transducer 20 (which drive pulse sets up a shear mode wave form in volume 18) and the time it takes for transducer 20 to generate an electrical signal indicating that the shear mode wave form has reflected off of a boundary condition in volume 18 (either the external boundary of volume 18 or an internal defect in volume 18) and returned to the transducer 20. The sonic echo signal generated by control-circuit 26 is indicative of this time differential and therefore indicative of the internal condition of the volume 18 at the point where the sonic wave form enter the volume. Sonic control circuits of this general type are well known in the prior art and will not be described herein.

As seen in FIGS. 3 and 4, the light transmission paths 22, 24 are located on either side of transducer 20. Each light transmission path 20, 22, includes a pair of optical fibers 32, 34 which form part of respective color intensity detectors 36, 38. The structure of color intensity detector 36 is illustrated in FIG. 5. As shown therein, color intensity detector 36 detects the intensity of color A on bichromatic screen 30 and therefore detects the position of portable sensor 16 along the X direction of screen 10 (see FIG. 1).

White light generated by a light source 40 is transmitted by optical fiber 32 onto bichromatic screen 10 at a location adjacent the remaining optical fiber 34. The ends of each optical fiber 32, 34 are preferably cut at an angle to ensure that a large percentage of the light emitted by optical fiber 32 will be received by optical fiber 34. The light received by optical fiber 34 is transmitted through a color filter 42 to a photodetector 44. Filter 42 filters out B color light. As such, the intensity of the light applied to photodetector 44 will vary as a function of the intensity of color A on the screen 10 in the area adjacent the ends of optical fibers 32, 34. As such, the intensity of the light appearing at the output of filter 42 is indicative of the position of a light transmission path 22, and therefore the position of portable sensor 16 along the X direction of screen 10.

Photodetector 44, which may be a photocell or other light sensitive device, generates an output signal indicative of the magnitude of the light appearing at the output side of filter 42. The signal is applied to an amplifier 46 which generates an X output signal indicative of the location of light transmission path 22 along the X axis of screen 10.

The structure and operation of color intensity detector 38 is identical to that of detector 36 with the exception that the filter 42 will filter out all A color light. As a result, color detector 38 generates a Y output signal which is indicative of the position of sensor 16 along the Y axis of screen 10. The X and Y output signals generated by color detectors 36, 38 together define the location of portable sensor 16 with respect to bichromatic screen 10, and therefore with respect to volume 18.

Reviewing the foregoing, color intensity detectors 36 and 38 generate output signals X and Y which are indicative of the position of sensor 16 with respect to screen 10 along the X and Y directions, respectively, and sonic control circuit 26 generates ultrasonic echo data signals indicative of the condition of volume 18 at the location indicated by the X and Y outputs of detectors 36 and 38, respectively. In the preferred embodiment, these three signals are applied to a microcomputer 42 which analyzes the signals and stores them in a memory 44. In a simple application, microcomputer 42 will convert the X and Y outputs of color intensity detectors 36 and 38, respectively, into an address signal unique to the position of portable sensor 16 with respect to screen 10. In this regard, microcomputer 42 divides screen 10 up into a plurality of discrete locations, each of which has a unique X and Y coordinate. Microcomputer 42 examines the X and Y outputs of detectors 36 and 38 and determines which discrete location on screen 10 these outputs correspond to. Microcomputer 42 then generates an address signal which is unique to this location and applies it to memory 44 via line 46. Microcomputer 42 also applies a digital signal to memory 44 on line 48 which signal is indicative of the information contained in the ultrasonic echo data signal generated by sonic control circuit 26. As such, microcomputer 42 will store the ultrasonic echo data signal appearing in the output of sonic control circuit 26 in that memory location of memory 44 which corresponds to the position of portable sensor 16 with respect to screen 10. If portable sensor 16 is moved across the entire face of screen 10, memory 44 will contain information regarding the internal structure of the entire volume 18 (assuming that screen 10 is at least relatively as big as the volume 18).

In addition to storing the information concerning the internal structure of volume 18 in memory 44, microcomputer 42 preferably displays this information on an output device 50. Output device 50 may be a simple printer which merely reads out a number corresponding to the echo time required for the sonic pulse generated by transducer 20 to reach the boundary condition in volume 18 and return to transducer 20 for each discrete position on screen 10. In a more sophisticated embodiment of the invention, output device 50 can be a CRT display which displays a pictorial representation of the internal structure of volume 18. The input information to the CRT display would be generated by microcomputer 42 as a function of the information contained in memory 44 in accordance with well known microcomputer techniques. Similarly, output device 50 can be a plotting device which produces a graphical representation of the internal structure of volume 18.

In the foregoing embodiment, only two color sensors 36 and 38 are used. Since the two light transmission paths 22, 24 of the sensors must be spaced apart from each other and from ultrasonic transducer 24, their outputs will positively locate the position of the transmitted ultrasonic beam only when the angular orientation of sensor 16 is at a preset orientation with reespect to the X-Y axis. This orientation may be referred to as the "perfect square". When moving the transducer across the two color screen, it may be angularly rotated with respect to the X-Y axis. Such an orientation is illustrated in FIG. 7. In order to compensate for this rotation, a third color intensity detector 52 may be used. Such a detector is illustrated in phantom in FIG. 2. The structure of this detector will be identical to that of detector 36 and will include a filter 42 which does not pass color B. As shown in FIG. 6, detector 52 will include a light transmission path 54 which is located to the right of light transmission path 22 as illustrated in FIG. 6. When sensor 16 is oriented at the "perfect square" with respect to screen 10, the output of detector 52 will be identical to the output of detector 36 (these two detectors dictating color A). Whenever the sensor 16 is off the "perfect square", the output of detectors 36, 52 will be different and, in fact, will indicate the angular orientation of sensor 16 with respect to screen 10.

As shown in FIG. 2, the output of color A detector 52 is applied to microcomputer 42 along with the output of detectors 36 and 38. Microcomputer 42 uses these three inputs to determine the exact orientation of sensor 16 with respect to screen 10 and adjusts the address signals applied to memory 44 accordingly.

As should be clear from the foregoing, it is necessary to scan the portable sensor 16 across the entire face of screen 10 in order to ensure that information containing the entire internal structure of volume 18 is stored in memory 44. Accordingly, microcomputer 42 preferably includes circuitry which indicates when the entire memory 44 is filled. This condition will only occur when the entire surface of screen 10 has been scanned. Alternatively, microcomputer 42 can control the operation of a CRT display which is initially all one color (i.e. black) and which is changed to a second color (i.e. white) at each location on a CRT screen corresponding to a location on screen 10 over which portable sensor 16 has been scanned. The operator of sensor 16 can ensure that he has scanned the entire screen 10 by continuing to move the sensor 16 until the entire face of the CRT tube has changed to the second color.

The present invention may be embodied in other specific forms without departing from the spirit or essential attributes thereof and, accordingly, reference should be made to the appended claims, rather than to the foregoing specification as indicating the scope of the invention.

What is claimed is:

1. An ultrasonic scanning system, comprising:
   bichromatic screen means having one surface colored with first and second colors, the intensity of said first color varying in a selected manner along a first direction on said surface, and the intensity of said second color varying in a second selected manner along a second direction on said surface oblique to said first direction;
   portable ultrasonic transducer means movable with respect to said screen means;
   means for causing said transducer means to repeatedly transmit ultrasonic signals through said screen means and to receive ultrasonic signals reflected off an object being scanned and located behind said screen means with respect to said transducer means; and
   detector means for measuring the respective intensities of said first and second colors at a point on said colored surface of said screen means corresponding to the lateral position of said ultrasonic transducer means with respect to said screen means.

2. The system of claim 1, wherein said first and second colors are complementary.

3. The system of claim 1, wherein said detector means comprises first and second color intensity detector means for measuring the intensities of said first and second colors, respectively, each of said color intensity detector means comprising:

light source means for generating a light beam for reflection from said surface of said screen means; and photoreceptor means for receiving a portion of said light beam after reflection thereof by said surface of said screen means.

4. The system of claim 3, wherein said detector means further comprises a third color intensity detector means for measuring the intensity of one of said two colors, said third color intensity detector means having the same structure as said first and second color intensity detector means.

5. The system of claim 1, further comprising sonic control circuit means for analyzing and storing ultrasonic signals received by said transducer means.

6. The system of claim 1, further including means for determining when said transducer means has scanned the entire surface of said bichromatic screen means.

7. The system of claim 6, wherein said determining means includes a display for indicating which portions of said bichromatic screen means has already been scanned.

* * * * *